United States Patent [19]

Yoshida et al.

[11] 4,278,569
[45] * Jul. 14, 1981

[54] 2,2,3-TRIMETHYL-3-CYCLOPENTEN-1-YLALKYL, ALKENYL AND ALKYLIDENE, CYCLOHEXANOLS, ORGANO-LEPTIC USES THEREOF IN PERFUME COMPOSITIONS, COLOGNES AND PERFUMED ARTICLES

[75] Inventors: Takao Yoshida, West Long Branch; Braja D. Mookherjee, Holmdel; Venkatesh Kamath, Red Bank; John B. Hall, Rumson, all of N.J.; William I. Taylor, Hertfordshire, England; Frederick L. Schmitt, Holmdel, N.J.

[73] Assignee: International Flavors & Fragrances Inc., New York, N.Y.

[ * ] Notice: The portion of the term of this patent subsequent to Dec. 23, 1997, has been disclaimed.

[21] Appl. No.: 149,650

[22] Filed: May 14, 1980

Related U.S. Application Data

[60] Continuation-in-part of Ser. No. 23,322, Mar. 22, 1979, Pat. No. 4,241,228, which is a division of Ser. No. 932,677, Aug. 10, 1978, Pat. No. 4,173,585.

[51] Int. Cl.$^3$ .......................... C07C 31/13; A61K 7/46
[52] U.S. Cl. .................... 252/522R; 568/316; 585/23; 424/59; 424/69; 424/70; 252/89.1; 252/8.6
[58] Field of Search .......................... 568/816; 585/23; 252/522

[56] References Cited

U.S. PATENT DOCUMENTS

| | | | |
|---|---|---|---|
| 3,527,816 | 9/1970 | Norell | 568/816 |
| 3,763,240 | 10/1973 | Solomon | 568/816 |
| 3,937,723 | 2/1976 | Schultze-Elte | 252/522 R |
| 4,052,341 | 10/1977 | Naipower et al. | 252/522 R |
| 4,088,681 | 5/1978 | Baumann et al. | 252/522 R |

Primary Examiner—Natalie Trousof
Assistant Examiner—James H. Reamer
Attorney, Agent, or Firm—Arthur L. Liberman

[57] ABSTRACT

Described are perfume and fragrance compositions and perfumed articles including soaps, detergents, powders as well as colognes containing 2,2,3-trimethyl-3-cyclopenten-1-ylalkyl, alkenyl and alkylidene, cyclohexanois, having the generic structure:

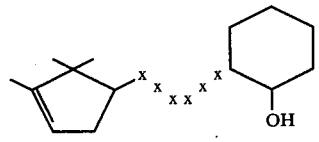

wherein at least one of the lines +++ is a carbon-carbon single bond and the other of the lines ++++ is either a carbon-carbon single bond or a carbon-carbon double bond, which imparts thereto woody, sandalwood aromas.

4 Claims, 6 Drawing Figures

GLC PROFILE FOR EXAMPLE I.

GLC PROFILE FOR EXAMPLE I, FRACTION 3.

NMR SPECTRUM FOR EXAMPLE I.

GLC PROFILE FOR EXAMPLE II.

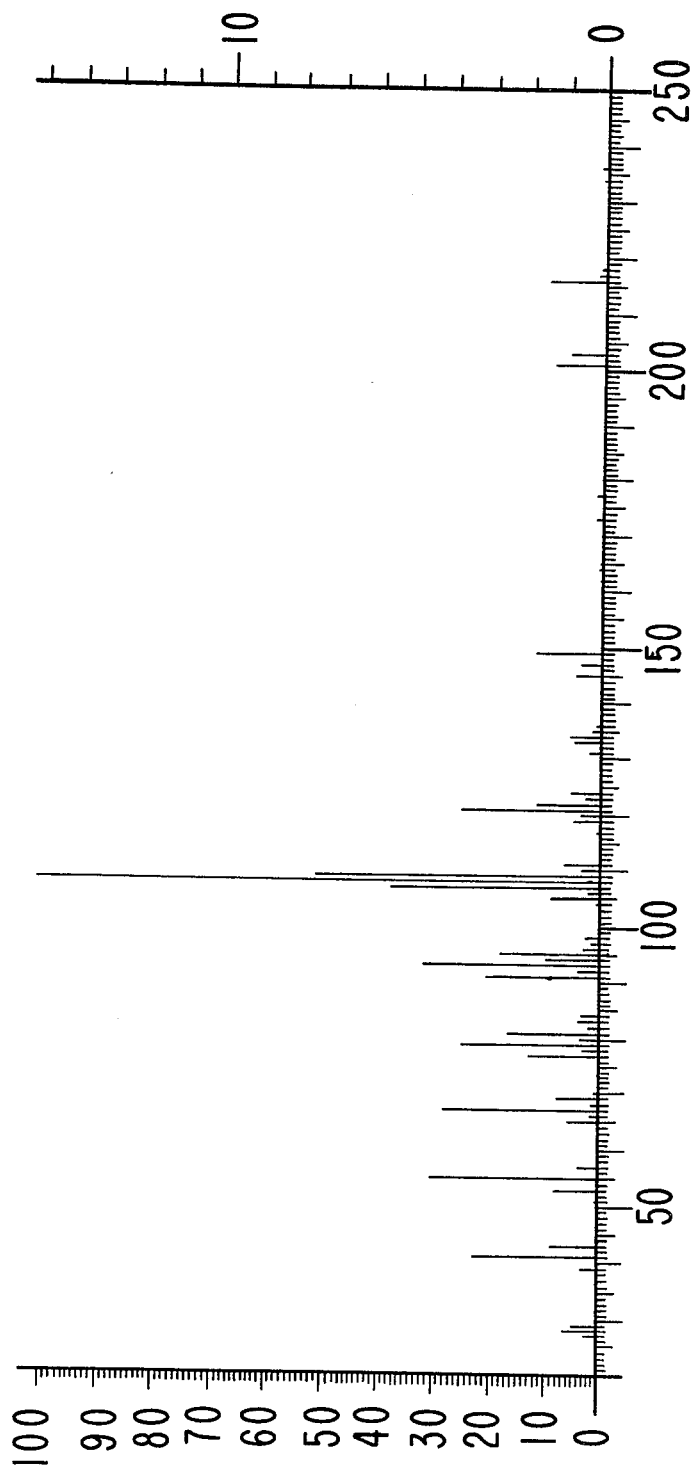
FIG. 6 MASS SPECTRUM FOR EXAMPLE II(B).

2,2,3-TRIMETHYL-3-CYCLOPENTEN-1-YLALKYL, ALKENYL AND ALKYLIDENE, CYCLOHEXANOLS, ORGANO-LEPTIC USES THEREOF IN PERFUME COMPOSITIONS, COLOGNES AND PERFUMED ARTICLES

This application is a continuation-in-part of application for U.S. Pat. Ser. No. 23,322 filed on Mar. 22, 1979, now U.S. Pat. No. 4,241,228 issued on Dec. 23, 1980 which, in turn, is a divisional of application for U.S. Pat. Ser. No. 932,677 filed on Aug. 10, 1978, now U.S. Pat. No. 4,173,585 issued on Nov. 6, 1979.

BACKGROUND OF THE INVENTION

There is a continuing search for materials having desirable fragrance properties. Such materials are used either to replace costly natural materials or to provide new fragrances of perfumed types which have not heretofore been available. Especially desirable qualities for substances havng interesting fragrances such as sandalwood-type fragrances are stability and persistence, particularly in a wide variety of perfumed articles (e.g. soaps, detergents and powders) perfumed compositions and colognes, ease of manufacture and intensity of aroma.

Furthermore, according to Guenther [E. Guenther, "The Essential Oils," Vol. V. page 173, D. Van Nostrand Co., Inc., New York (1952)], East Indian sandalwood oil "has been perhaps one of the most precious perfumery materials from antiquity down to modern times, and its popularity has shown no signs of waning." This oil is widely used in perfumery, and would be even more widely used except for its limited supply and high cost.

As is well known, a need exists for synthetic substances which can be used as sandalwood substitutes or extenders. It would be most desirable to be able to synthetically provide the major odorant compounds of the natural sandalwood oil, i.e., alpha-santalol and beta-santalol, but no commercially feasible route to these chemicals is known at this time.

It would be even more desirable to provide a synthetic compound which would have many of the desirable odor qualities of a fine East Indian sandalwood oil, yet not have the potentially labile primary allylic alcohol group present in the natural santalols. A compound which would be more resistant to acidic or oxidative decomposition as well as being base stable could be even more versatile than sandalwood oil itself.

There is no obvious explanation why only slight chemical changes should have such a dramatic effect on odor intensity other than to invoke the general unreliability of odor structure relationships. Why the addition or removal of a methyl group, the removal of a double bond or the mere moving of a methyl group would essentially destroy more than 90% of the odor intensity rather than merely cause subtle odor differences comparable to the subtle chemical differences cannot be explained by any theoretical concepts in the known art.

U.S. Pat. No. 4,052,341, issued on Oct. 4, 1977 provides a sandalwood type aroma imparting material having one of the structures:

TABLE I

| Name | Structure |
|---|---|
| 3-Methyl-5-(2,2,3-trimethylcyclopent-3-en-1-yl)pentan-2-ol | 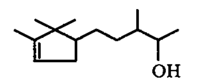 |
| 3-Methyl-5-(2,2,3-trimethylcyclopentan-1-yl)pentan-2-ol | 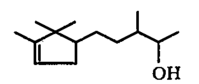 |
| 5-(2,2,3-Trimethylcyclopent-3-en-1-yl)pentan-2-ol | |
| 6-(2,2,3-Trimethylcyclopent-3-en-1-yl)hexan-3-ol | |
| 4-Methyl-6-(2,2,3-trimethylcyclopent-3-en-1-yl)hexan-3-ol | 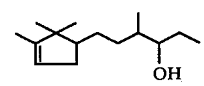 |
| 3-Ethyl-5-(2,2,3-trimethylcyclopent-3-en-1-yl)pentan-2-ol | 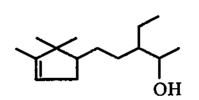 |
| 3-Methyl-5-(2,2,3-trimethylcyclopent-3-en-1-(R)-yl)pentan-2-ol | 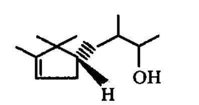 |
| 3-Methyl-5-(2,2,3-trimethylcyclopent-3-en-1-(S)-yl)pentan-2-ol | 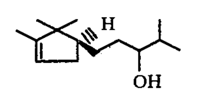 |
| 3-Methyl-5-(2,2,3-trimethylcyclopent-3-en-1-yl)pent-3-en-2-ol | 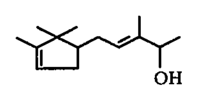 |

These materials are produced according to the reaction schemes:

TABLE II

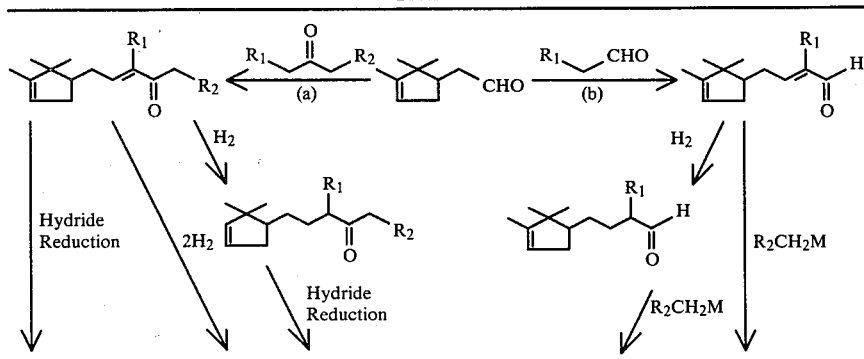

TABLE II-continued

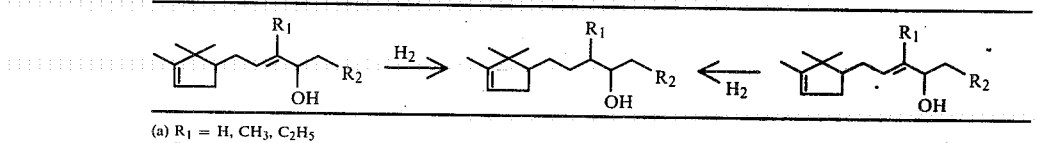

(a) $R_1$ = H, $CH_3$, $C_2H_5$
$R_2$ = H, $CH_3$

East Germany Pat. No. 68,936 discloses for use in the sandalwood area a compound having the structure:

Furthermore, Chemical Abstracts Volume 72, 125008b sets forth a genus for the East German 68,936 encompassing the following group of compounds:

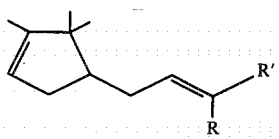

wherein R=$CH_2OH$, $CHCH_3OH$ and R'=H,$CH_3$ or $C_2H_5$.

The compounds of our invention, defined according to the generic structure:

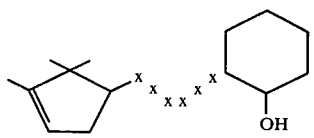

wherein at least one of the lines + + + + is a carbon-carbon single bond and the other of the lines + + + + is either a carbon-carbon single bond or a carbon-carbon double bond, which imparts thereto woody, sandalwood aromas, have unobvious and unexpected properties insofar as their perfumery properties are concerned.

Chemical Abstracts 92: 93595g is an Abstract of Japanese Kokai (Published Patent Application) No. 79,125,645, assigned to the Takasago Perfumery Co., Ltd. and indicates the usefulness in perfumes of, inter alia, the compound having the structure:

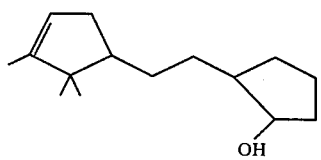

and indicates that this compound is produced using the reduction of the corresponding unsaturated ketone having the structure:

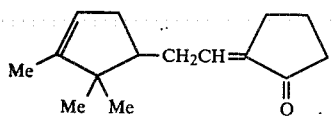

by means of hydrogenation over a copper chromite catalyst in isopropyl alcohol containing a small quantity of potassium hydroxide at 120° C. The publication date of the subject Japanese Kokai 79,125,645 is Sept. 29, 1979 which is subsequent to the filing date of the parent application Ser. No. 932,677 filed on Aug. 10, 1978. In addition, the compounds of our invention have unexpected, unobvious and advantageous properties with respect to the lower methylene homologues of Japanese Kokai No. 79,125,645.

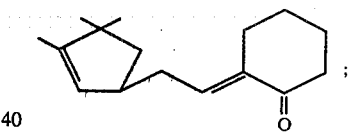

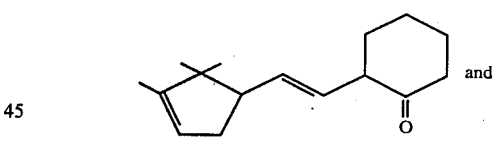

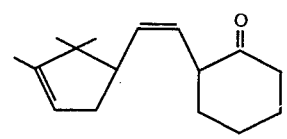

Figure 2:
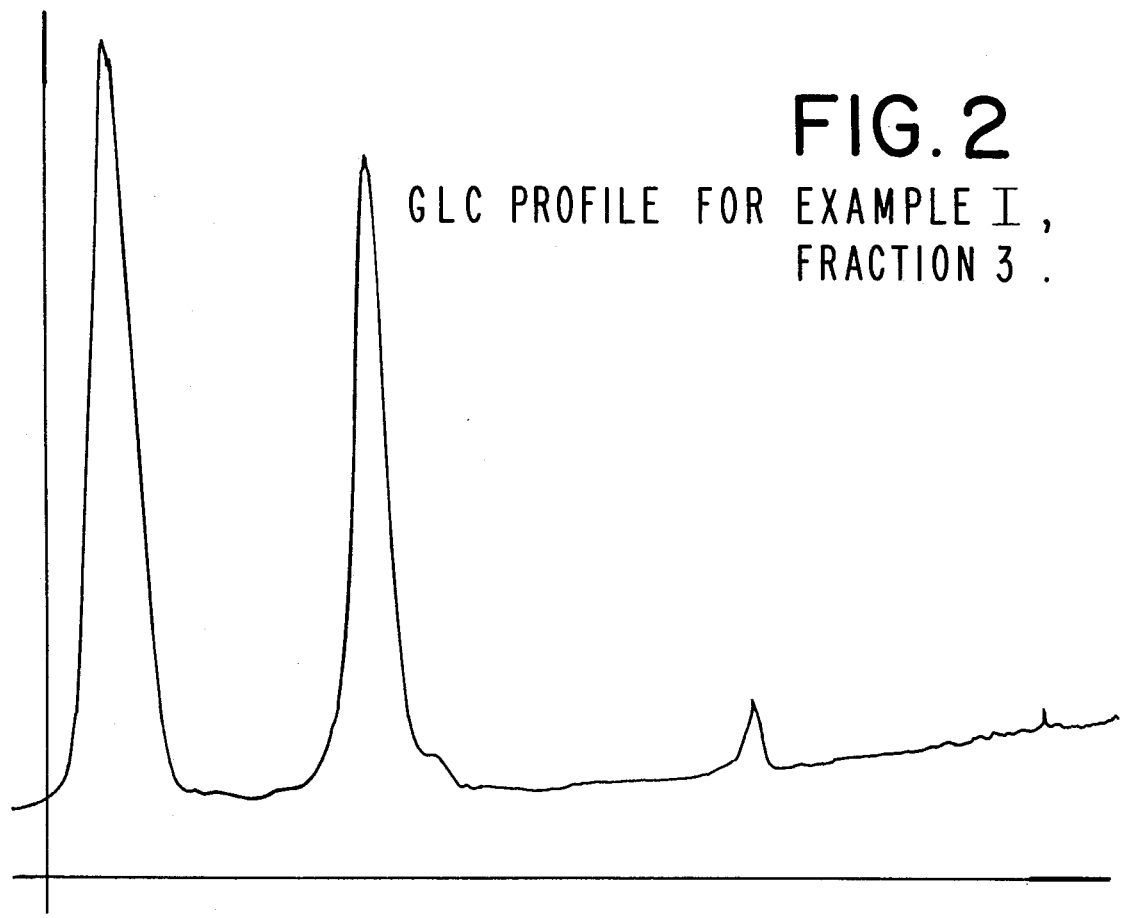

FIG. 2 is the GLC profile for fraction 3 resulting from the fractional distillation of the reaction product of Example I which contains compounds having the structures:

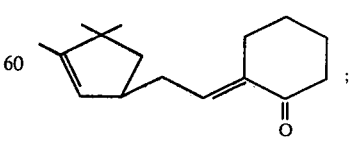

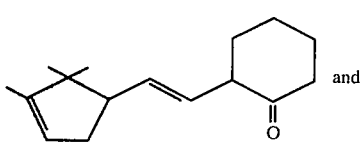

-continued

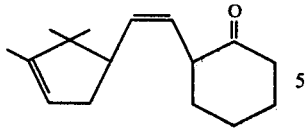

Figure 3:
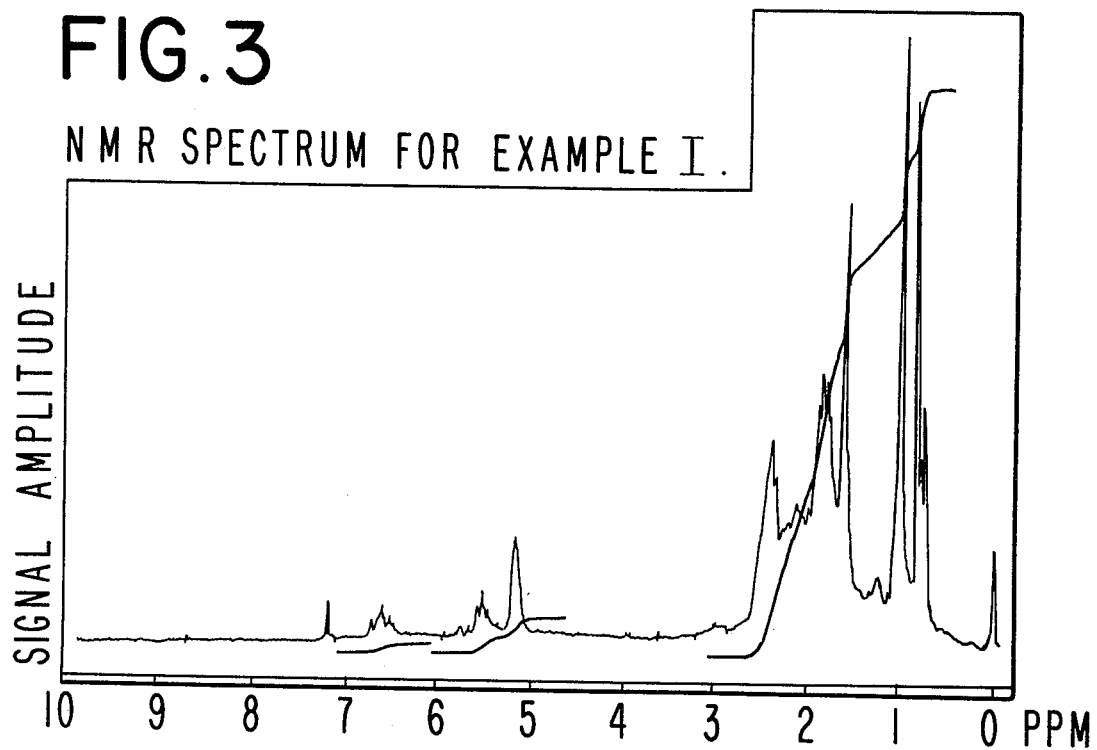

FIG. 3 is the NMR spectrum for fraction 3 resulting from the fractional distillation of the reaction product of Example I having the compounds having the structures:

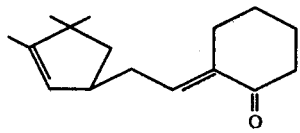

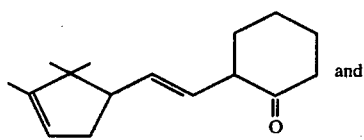 and

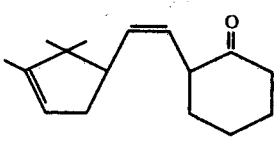

Figure 4:
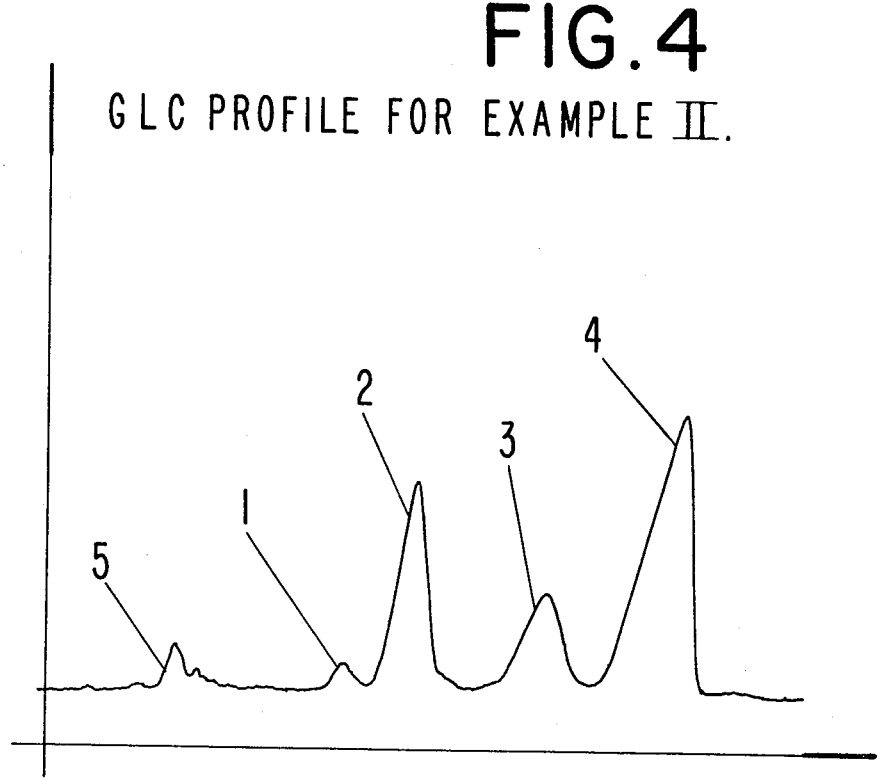

FIG. 4 is the GLC profile for the reaction product of Example II containing the compounds having the structures:

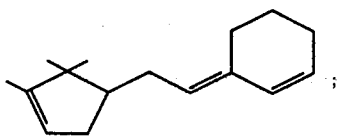

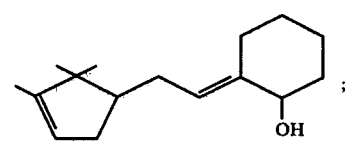

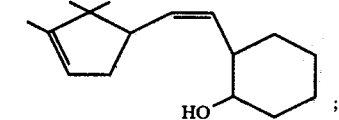

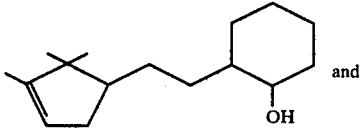 and

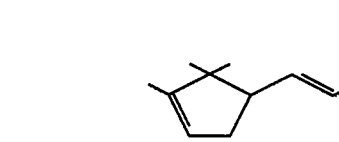

Figure 5:
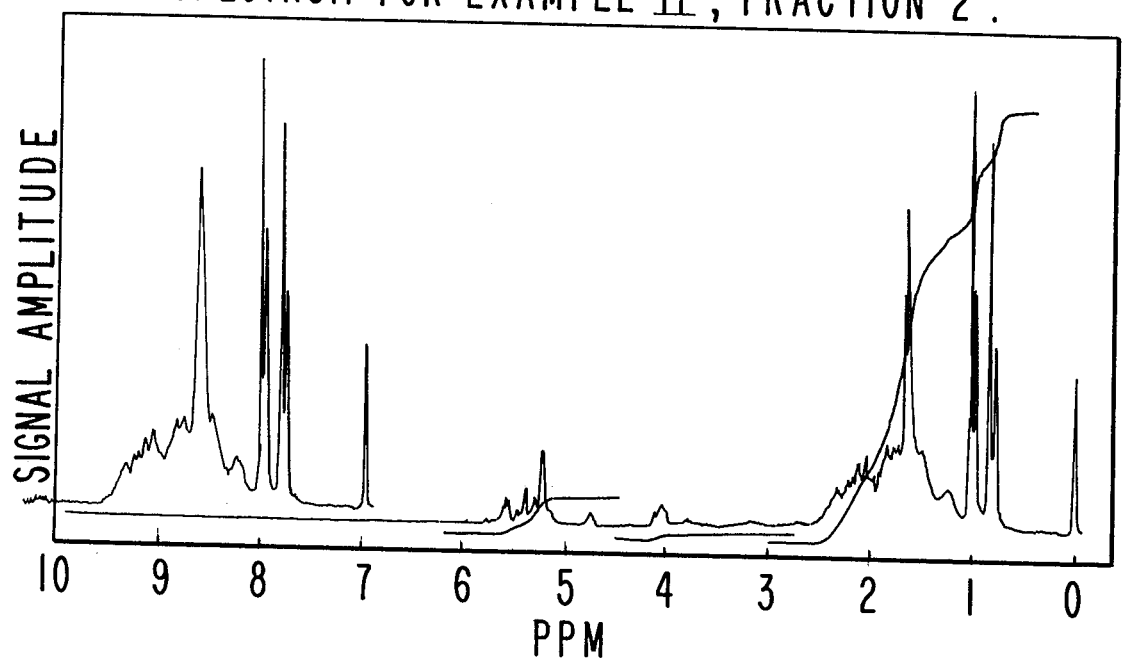

FIG. 5 is the NMR spectrum for fraction 2 resulting from the fractional distillation of the reaction product of Example II containing the compounds having the structures:

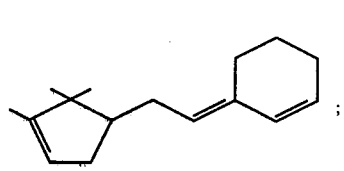

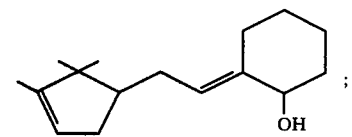

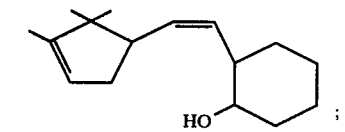

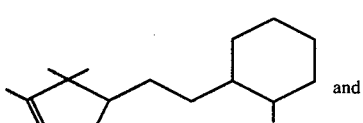 and

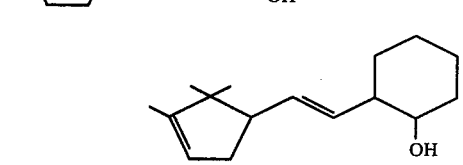

FIG. 6 is the mass spectrum for peak "3" of the GLC profile of FIG. 4, which peak contains the compounds having the structures:

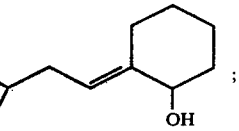

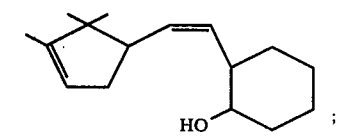

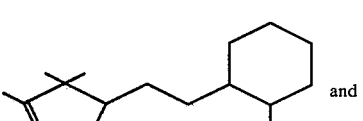 and

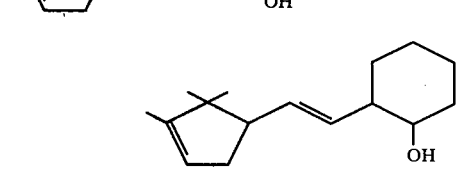

DETAILED DESCRIPTION OF FIG. 4

FIG. 4 is the GLC profile for the reaction product of Example II containing peaks which include compounds having the structures:

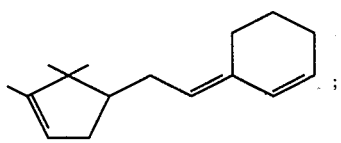

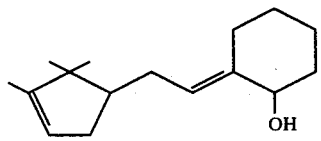

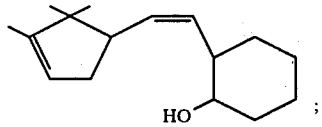

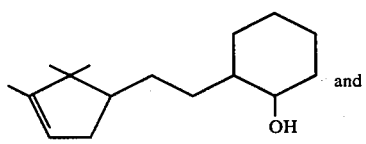

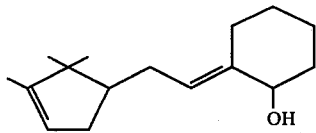

Peak "1" contains the compound, in an amount of approximately 2.8%, having the structure:

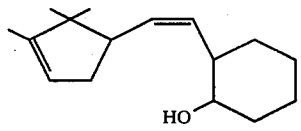

Peak "2" contains approximately 28.2% of the compound having the structure:

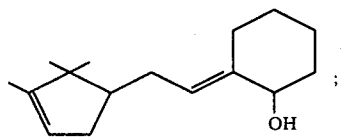

Peak "3", the peak containing the mixture of our invention, contains 16.6% of the compounds having the structures:

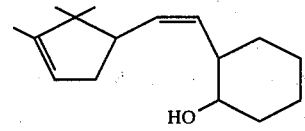

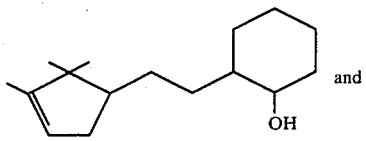

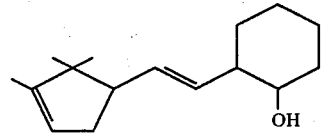

Peak "4" contains approximately 45.2% by weight of the compound having the structure:

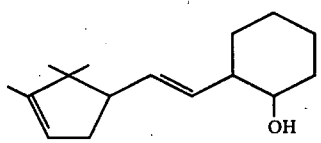

Peak "5" contains approximately 4.8% by weight of the compound having the structure:

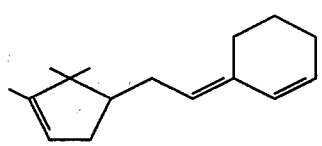

THE INVENTION

The invention comprises a novel compound defined according to the structure:

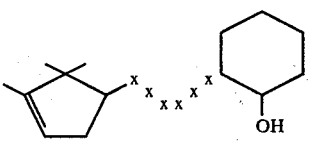

wherein at least one of the lines ++++ is a carbon-carbon single bond and the other of the lines ++++ is either a carbon-carbon single bond or a carbon-carbon double bond, which imparts thereto woody, sandalwood aromas.

The invention also comprises certain novel perfumed compositions, novel perfumed articles including solid or liquid anionic, cationic and zwitterionic detergents, cosmetic compositions, fabric softeners and fabric softener articles and novel colognes.

The compounds of our invention may be prepared by first preparing a mixture of ketones according to the reaction scheme:

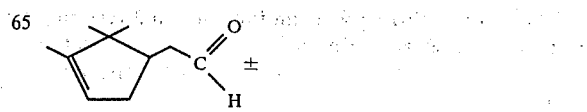

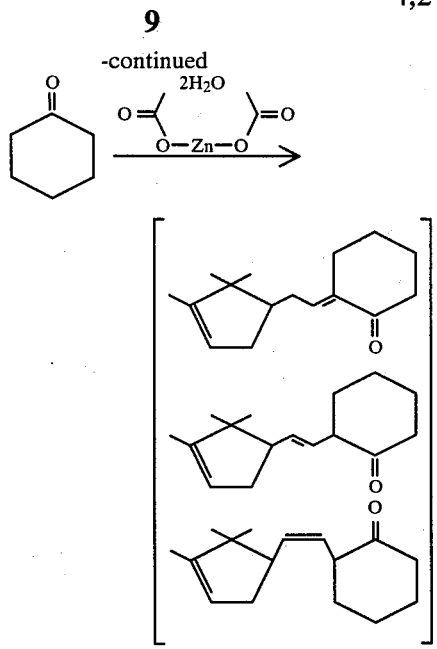

as more specifically set forth in U.S. Pat. No. 4,173,585 issued on Nov. 6, 1979, the parent case of the instant application or with regular aldol condensation catalysts, such as sodium hydroxide or potassium hydroxide.

The resulting ketone mixture is then subjected to reduction using alkaline metal borohydrides such as sodium borohydride or lithium aluminum hydride to produce a mixture of alcohols and hydrocarbons containing compounds having the structures:

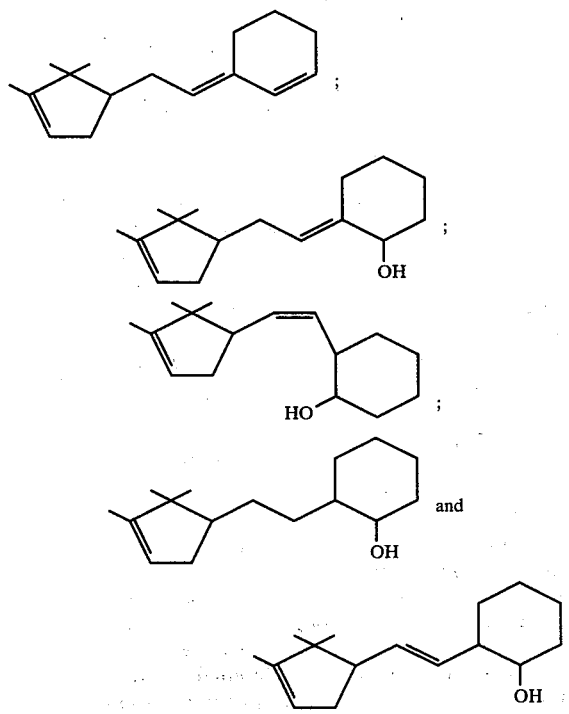

The reaction is to take place in the presence of an inert solvent such as anhydrous methanol, anhydrous ethanol or anhydrous isopropylalcohol. The temperature of reaction is between 0° C. and 40° C.; preferably between 15° C. and 30° C. The most convenient pressure to use is one atmosphere, however, higher pressures may be used without reduction in yield or conversion.

The concentration of alkaline metal borohydride or lithium aluminum hydride in the reaction mass may vary from 10 grams per liter up to 200 grams per liter with a preferred range of catalyst concentration of between 40 and 80 grams per liter of alkaline metal borohydride or lithium aluminum hydride.

The concentration of ketone reactant in the reaction mass may vary from 500 grams per liter up to 1000 grams per liter with a preferred range of from 700 up to 800 grams per liter.

The ratio of alkaline metal borohydride catalyst or lithium aluminum hydride catalyst to ketone reactant may vary from about 0.05:1 up to about 0.03:1 with a preferred range of weight ratios of catalyst: ketone reactant being from about 0.08:1 up to about 0.12:1.

The reduction reaction may be monitored using GLC techniques, if desired. At the end of the reaction, the reaction mass is "worked up" using standard physical "work up" procedures including extraction, neutralization, drying, fractional distillation and preparative vapor phase chromatography or preparative "GLC" (gas-liquid chromatography) and/or high pressure liquid chromatography ("HPLC") which high pressure liquid chromatography can be carried out on a large commercial scale.

The reaction for reducing the ketones may be shown schematically as follows:

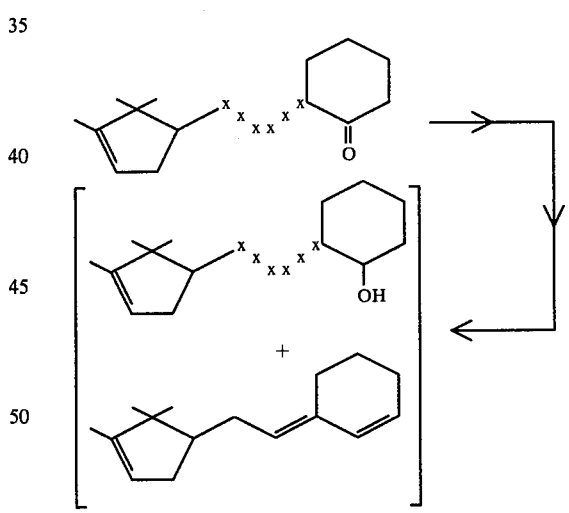

wherein at least one of the lines + + + + is a carbon-carbon single bond and the other of the lines + + + + is either a carbon-carbon single bond or a carbon-carbon double bond, which imparts thereto woody, sandalwood aromas.

The compounds having the structures:

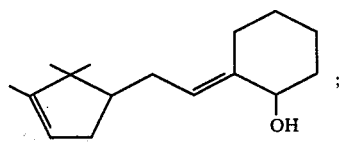

-continued

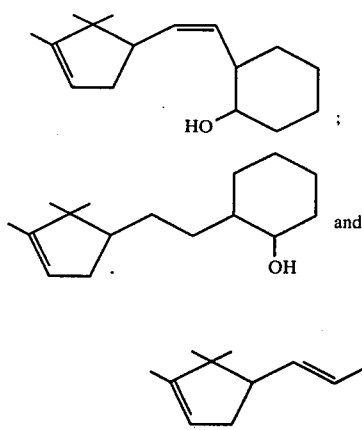

all have intense sandalwood aromas but the mixture of compounds obtained from peak "3" of the GLC profile having the structures:

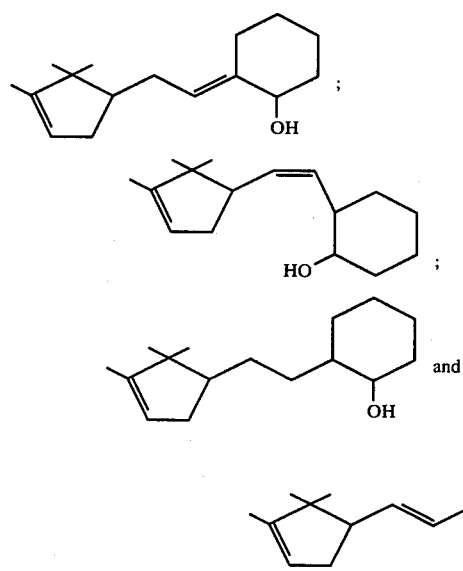

has the most intense sandalwood note which is attributable to the compound having the structure:

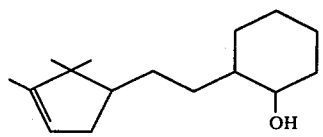

The compound having the structure:

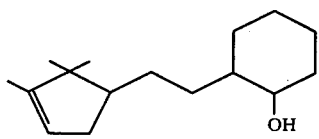

may be further purified and separated from the remainder of the mixture of compounds by further preparative GLC techniques, including high pressure liquid chromatography.

The mixture of compounds having the structures:

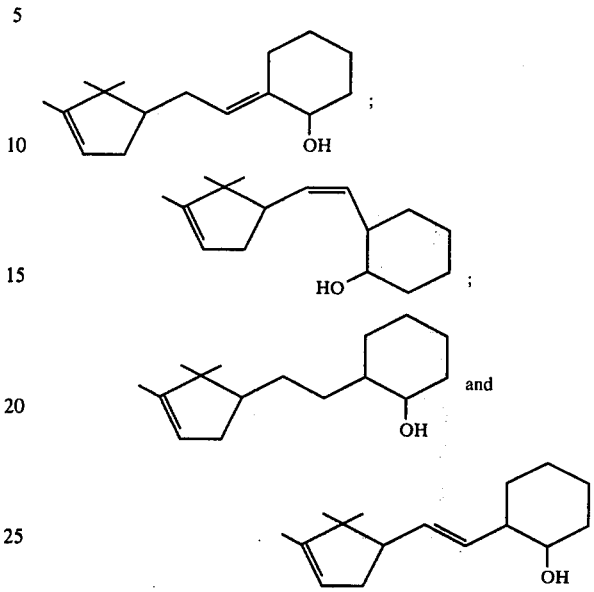

obtained from peak "3" of the GLC profile as set forth in FIG. 4 (hereinafter referred to as "cyclohexanol derivatives") of our invention can be added to perfume compositions as pure compounds or can be added to mixtures of materials in fragranced imparting compositions as can the compound having the structure:

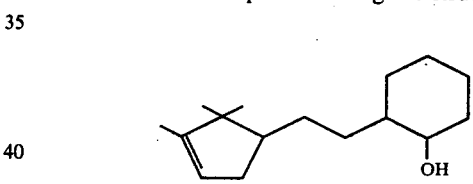

be so added, in order to provide a desired fragrance character to a finished perfume material. The perfume and fragrance compositions obtained according to our invention are suitable in a wide variety of perfumed articles and can also be used to enhance, modify or reenforce natural fragrance materials. It will thus be appreciated that the cyclohexanols derivatives of our invention is (are) useful as olfactory agent(s) and fragrance(s).

The term "perfume composition" is used herein to mean a mixture of compounds including, for example, natural oils, synthetic oils, alcohols other than those covered by the alcohols produced according to this invention, aldehydes, alcohols other than those alcohols produced according to the processes of our invention, ketones other than those ketones produced according to the processes of our invention, esters, lactones, nitriles and frequently hydrocarbons which are admixed so that the combined odors of the individual components produce a pleasant or desired fragrance. Such perfume compositions usually contain (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling fresh-smelling materials. Such perfume compositions of our invention can be used in conjunction with carriers, vehicles, solvents, dispersants, emulsifiers, surface-active agents, aerosol propellants and the like.

In perfume compositions the individual components contribute their particular olfactory characteristics, but the overall effect of the perfume composition will be the sum of the effect of each ingredient. Thus, the cyclohexanols derivatives of our invention can be used to alter, augment, modify or enhance the aroma characteristics of a perfume composition or a perfumed article, for example, by highlighting or moderating the olfactory reaction contributed by another ingredient of the composition.

The amount of one or more of the cyclohexanol derivatives of our invention which will be effective in perfume compositions depends upon many factors, including the other ingredients, their amounts and the effects which are desired. It has been found that perfume compositions containing as much as 40% or as little as 0.1 ppm (0.00001%) by weight of the mixtures or compounds produced according to the process of our invention or the mixtures or compounds of this invention or even less can be used to impart a strong long-lasting woody sandalwood aroma having an important urine character necessary in the sandalwood note to soaps, cosmetics, solid or liquid anionic cationic or nonionic or zwitterionic detergents, cosmetic powders, fabric softener compositions, fabric softerner articles (such as BOUNCE ® a Registered Trademark of the Procter and Gamble Company of Cincinnati, Ohio) and other products. The amount employed will depend upon considerations of cost, nature of the end product, the effect desired in the finished product and the particular fragrance sought.

One or more of the cyclohexanol derivatives of our invention as disclosed herein can be used alone, in a fragrance modifying composition or in a perfume composition as an olfactory component in detergents (anionic detergents, cationic detergents, nonionic and zwitterionic detergents) and soaps; space deodorants; perfumes; colognes, bath preparations such as bath oil, bath salts; hair preparations such as lacquers, brilliantines, pomades, and shampoos; cosmetic preparations such as cremes, deodorants, hand lotions, sun screen; powders such as talcs, dusting powders, face powders and the like. When one or more of the cyclohexanol derivatives of our invention is used in perfumed articles such as the foregoing, it can be used in amounts of from about 0.5 ppm (0.00005%) or lower. Generally it is preferred not to use less than about 0.2 ppm and no more than about 3% in the finished perfumed article, since the use of too much will tend to unbalance the total aroma and will needlessly raise the cost of the article.

The following examples serve to illustrate embodiments of the invention as it is now preferred to practice it. It will be understood that these examples are illustrative and the invention is to be restricted thereto only as indicated in the appended claims.

EXAMPLE I

PREPARATION OF CAMPHOLENYLIDENE CYCLOHEXANONE

REACTION:

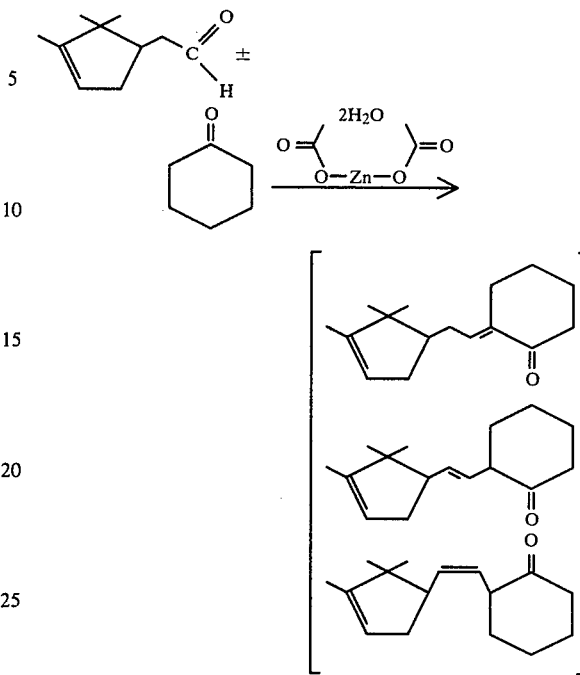

Into a 2 liter autoclave capable of being pressurized to 20 atmospheres are charged 152 grams of (1.0 moles) campholenic aldehyde, 490 grams (5.0 moles) of cyclohexanone and 44 grams (0.2 moles) of zinc acetate dihydrate. The contents of the autoclave are heated to 180° C. and at a pressure of 160–170 psig for a period of 10 hours. At the end of the 10 hour period, the reaction mass is cooled and solids are filtered and washed neutral with sodium bicarbonate and aqueous sodium chloride.

The resulting reaction product is distilled through a splash column containing saddle stones yielding the following fractions:

| No. | Vapor Temp (°C.) | Liquid Temp (°C.) | Vac. mm Hg | Weight of Fraction |
|---|---|---|---|---|
| 1 | 31–94 | 70–157 | 3.0 | 22.7 |
| 2 | 94–128 | 157–168 | 3.0 | 5.1 |
| 3 | 128–130 | 168–200 | .8 | 53.5 |
| 4 | 130–195 | 200–227 | .8 | 59.8 |

Figure 1:
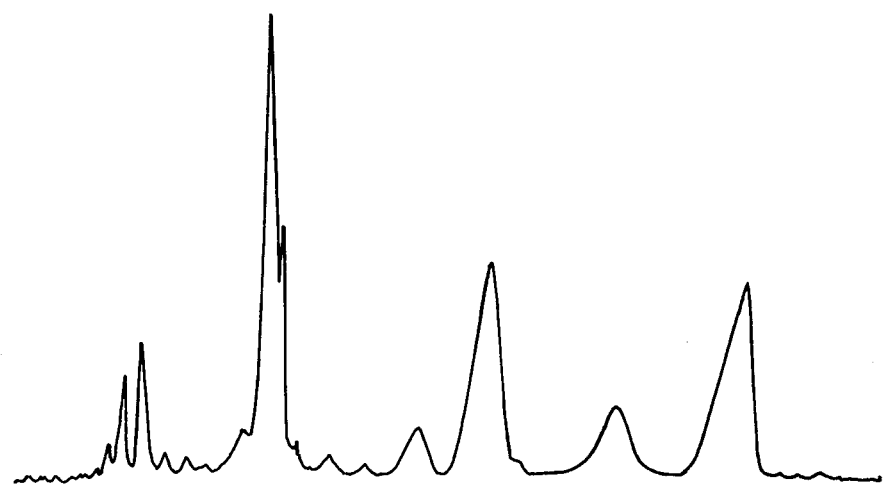
FIG. 1 is the GLC profile for the reaction product of Example I consisting of compounds having the structures.

53.5 grams of product is collected. The GLC profile for this product is set forth in FIG. 1. Fraction 3 resulting from the fractional distillation has a GLC profile as set forth in FIG. 2. The NMR spectrum for fraction 3 is set forth in FIG. 3. Fraction 3 contains the isomers:

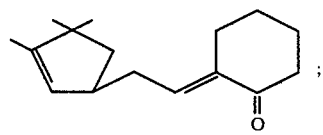
;

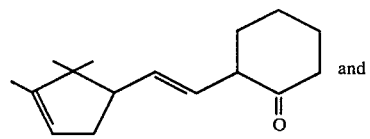
and

-continued

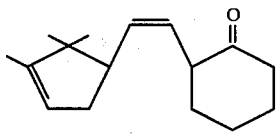

EXAMPLE II

PREPARATION OF CYCLOHEXANOL DERIVATIVES OF INVENTION

REACTION:

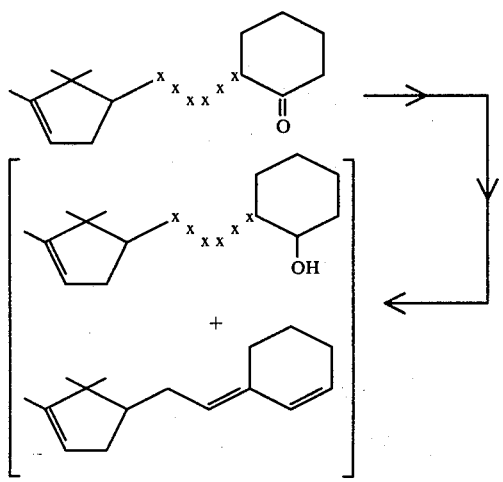

wherein at least one of the lines + + + + is a carbon-carbon single bond and the other of the lines + + + + is either a carbon-carbon single bond or a carbon-carbon double bond.

In a 250 ml three-necked reaction flask is placed a solution of 52 grams of campholenylidene cyclohexanone, fraction 3 according to Example I (0.22 moles) in 50 ml of anhydrous methanol. To this solution 3.5 grams (0.092 moles) of sodium borohydride dissolved in 20 ml of anhydrous methanol is added over a period of 30 minutes while maintaining the reaction mixture at 20°–23° C. The reaction mass is then stirred at room temperature for a period of 4 hours. 10% acetic acid is added dropwise (100 ml) over a period of 5 minutes at about 15° C. The reaction mass is then stirred for another 10 minutes and the aqueous layer is separated from the organic layer. The organic layer is washed with 100 ml 10% acetic acid and washed neutral with saturated sodium bicarbonate. The reaction mass is then distilled on a micro-vigreaux column yielding the following fractions:

| No. | Vapor Temp (°C.) | Liquid Temp (°C.) | Vac mm Hg. | Wt. of Fraction |
|---|---|---|---|---|
| 1 | 121–135 | 149–149 | 3 | 2 |
| 2 | 135–143 | 149–158 | 3 | 14.9 |
| 3 | 143 | 158–162 | 3 | 11.8 |
| 4 | 143 | 162–173 | 3 | 7.1 |
| 5 | 143 | 173–320 | 3 | 6 |

FIG. 4 is the GLC profile for fraction 2 of the reaction product

FIG. 5 is the NMR spectrum for fraction 2.

FIG. 6 is the mass spectrum for peak "3" of the GLC profile of FIG. 4.

Fraction 2 of the distillation product above contains compounds having the following structures:

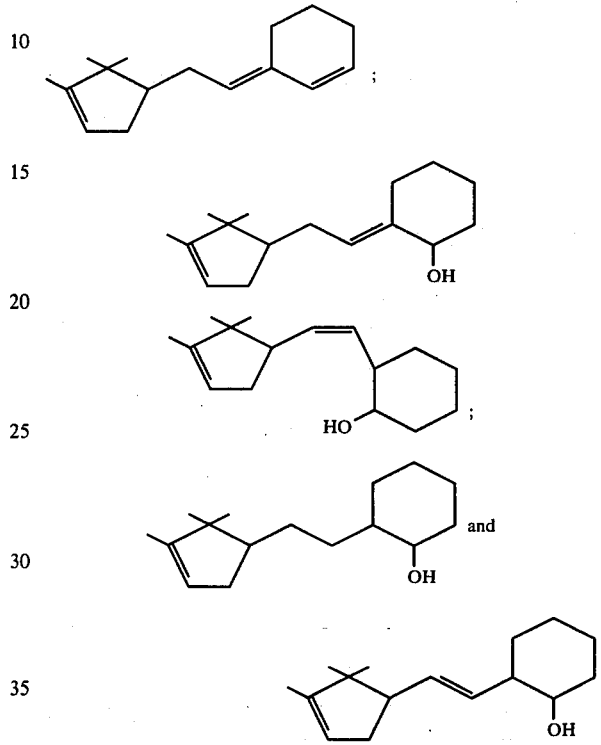

Peak "3" of the GLC profile of FIG. 4 contains compounds having the following structures:

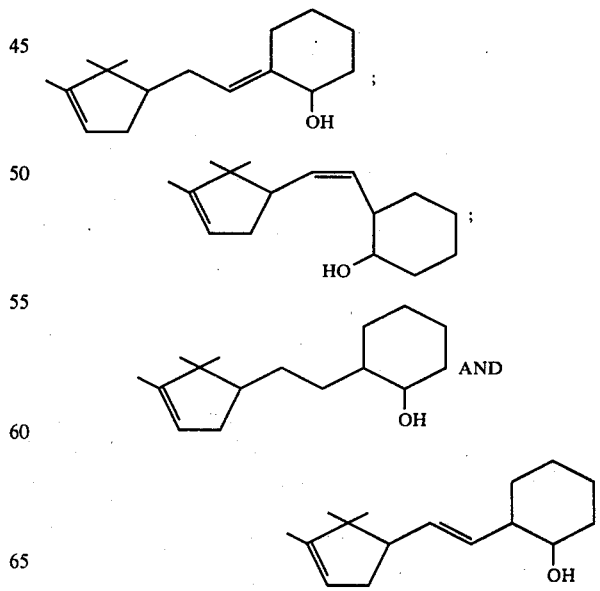

The compound having the structure:

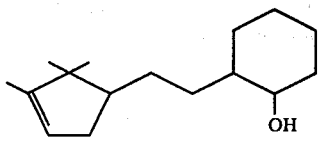

can be made by chromatographic techniques, including high pressure liquid chromatography yielding a compound having an extremely high intensity woody sandalwood note.

EXAMPLE III

SANDAL PERFUME FORMULATION

The following mixture is prepared:

| Ingredients | Parts by Weight |
| --- | --- |
| 1',2',3',4',5',6',7',8'-octahydro-2',3',8',8',-tetramethyl-2'-aceto-naphthone isomer mixture produced according to the process of Example VII of Application for U.S. Letters Pat. No. 434,948 filed on January 21, 1974 (now U.S. Pat. No. 3,911,018 issued on October 7, 1975). | 540 |
| Cedrenal - (A tricyclic sesquiterpinic aldehyde derived from cedrene, having the structure: <br><br> produced according to the process of U.S. Pat. Application No. 260,537 filed on June 7, 1972 (now U.S. Pat. No. 3,869,516, issued on March 4, 1975) (corresponding to published Dutch Appln. 7,307,849 laid open for public inspection on December 11, 1973). | 90 |
| Eugenol (1% in ethyl alcohol) | 54 |
| 2,5,5-trimethyl acetyl cycloheptane produced according to Example I of U.S. Pat. Application No. 349,180 filed on April 9, 1973 (now U.S. Pat. No. 3,869,411 issued on March 4, 1975). | 180 |
| Borneol (1% in ethyl alcohol) | 18 |
| Hexahydro-4,7-methanoindane-2-carboxaldehyde | 18 |
| Mixture of compounds having the structures: | 100 | produced according to Example II.

The mixture of compounds produced according to Example II imparts the woody, sandalwood-like note in a very intense manner with a subliminal urine background characteristic lending to the aroma a very natural-like sandalwood character.

EXAMPLE IV

PREPARATION OF A SOAP COMPOSITION

A total of 100 grams of soap chips produced from unperfumed sodium base toilet soap made by tallow and coconut oil are mixed with 1 gram of the perfume composition produced according to Example III until a substantially homogeneous composition is obtained. The soap composition manifests a characteristic "sandal cologne" aroma having the intense musky nuances. A similar sandal cologne aroma containing soap is produced using the compound having the structure:

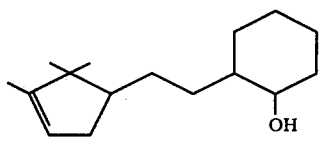

EXAMPLE V

PREPARATION OF A SOLID DETERGENT COMPOSITION

A total of 100 grams of a detergent powder as sold under the trademark "RINSO" ® are mixed with 0.15 grams of the perfume composition of Example III until a substantially homogeneous composition having a "sandal cologne" fragrance with musky aromas is obtained. A similar detergent is produced using the compound having the structure:

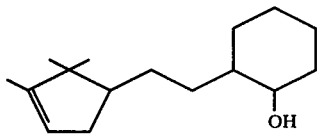

EXAMPLE VI

PREPARATION OF COLOGNE AND HANDKERCHIEF PERFUME

The perfume composition of Example III is incorporated into colognes having concentrations of 1.5%, 2.0%, 2.5%, 3.0%, 4.0%, and 5.0% in 70%, 75%, 80%, 85%, and 90% aqueous ethanol; and into handkerchief perfumes at concentrations of 10%, 15%, 20%, 25% and 30% (in 70%, 75%, 80%, 85% and 95% ethanol). The use of the composition of Example III affords a distinct and definite "sandal cologne" aroma having a warm sandalwood-like wood character with musky nuances to the handkerchief perfumes and to the colognes.

EXAMPLE VII

PERFUMED LIQUID DETERGENT

Concentrated liquid detergents with strong sandalwood aromas and musky backgrounds with woody nuances are prepared containing 0.10%, 0.15%, 0.20%, 0.25% and 0.30% of mixtures of compounds having the structures:

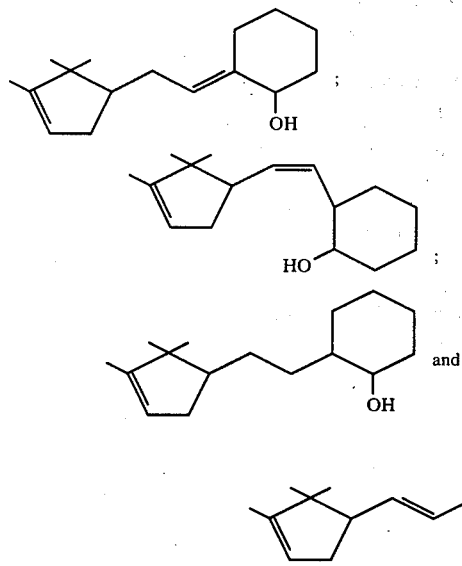

prepared according to Example III and also containing only the compound having the structure:

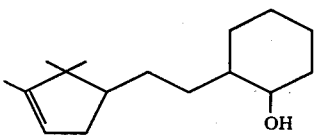

The liquid detergents are prepared by adding and homogeneously mixing the appropriate quantities of said mixture or said compound having the structure:

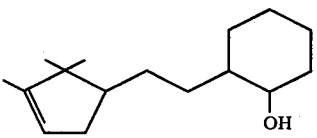

prepared according to Example II and the liquid detergents described according to British Pat. No. 1,092,149 containing 2% by weight ethyl/maleic anhydride copolymer (specific viscosity 0.5–1.0) and 0.42 weight percent methyl vinyl ethyl/maleic anhydride copolymer (specific viscosity 0.4) as stabilizer and 8% by weight of a sultaine detergent. The detergents all possess strong sandalwood aromas with woody and musky nuances, the intensities increasing with greater concentrations of compounds and mixtures prepared according to Example II. Similar effects are obtained using the perfumed composition of Example III.

EXAMPLE VIII

A cosmetic soap is prepared according to the procedure set forth in Japanese Patent 79/028-846 published on Sept. 19, 1979 and granted to Kawaken Fine Chemicals Ltd. The soaps are prepared with RNHCH$_2$CH(R$_1$)(OCH$_2$—CH$_2$)$_n$—P(O)(OX)OY (wherein R is 16 carbon acyl; R$_1$ is methyl; n is 12; X and Y equals RNCH$_2$CH(R$_1$)(OCH$_2$CH$_2$)$_n$.

The resulting material is combined with a basic soap material at the rate of 7% and is combined with the mixture of compounds prepared according to Example III, (peak "3" of the GLC profile) containing the compounds having the structures:

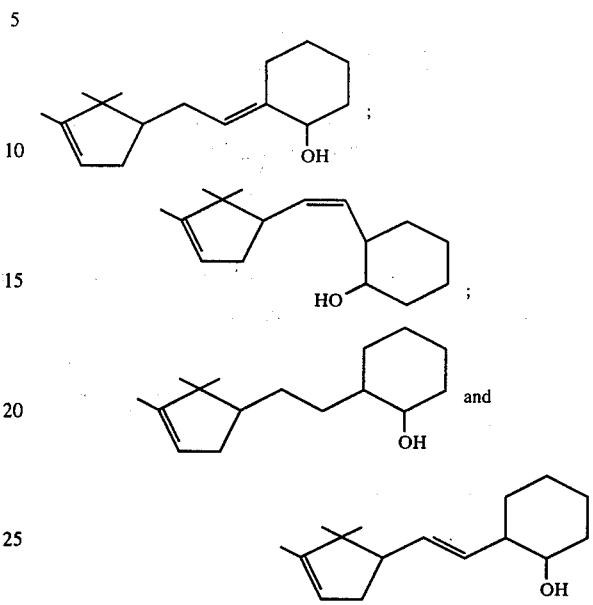

to provide a cosmetic soap having a sandalwood, woody aroma with a musky background.

EXAMPLE IX

PERFUMED TEXTILE FINISH

Hydrophilic polyurethanes for soil-resistant textile finishes are prepared from diisocyanates and compounds containing specific types of reactive hydrogen atoms according to Japanese Patent 79/34-435 published on Oct. 26, 1979 and assigned to the Rhone-Poulenc Industries. These textile finishes are pre-fragranced with the perfume compositions of Example III as well as with the compounds prepared according to Example II having the structures:

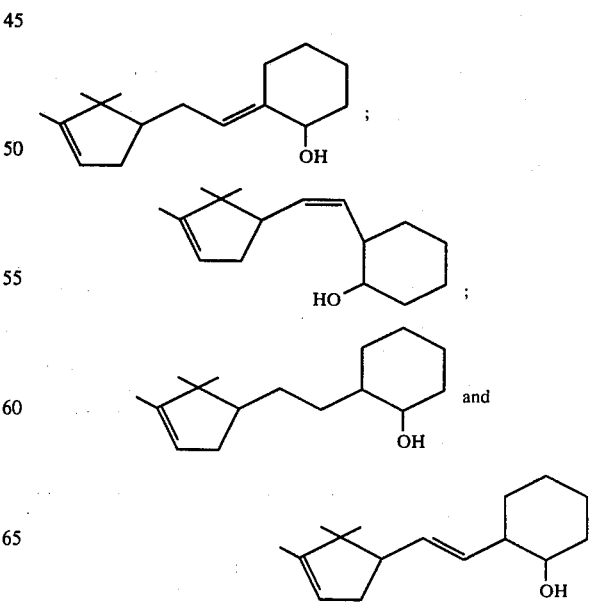

Thus, a hydrophilic polyurethane is obtained by reaction of 35 weight percent of tolylene diisocyanate; and 65 weight percent of a mixture of 75 weight percent of a compound having the formula R—(OCH$_2$H$_4$)$_n$—OH (where R is a 15 carbon hydrocarbon residue and n is such as the molecular weight is 6,500 and 25 weight percent of 1,4-butylene diol; and 1% by weight of a nitrogen containing compound with the formula R$_1$NX$_1$X$_2$ where R$_1$ is C$_5$ alkyl and X$_1$ and X$_2$ represent aminopentyl. The tertiary nitrogen atom compound R$_1$—NX$_1$X$_2$ is quaternised with the diisocyanate after the reaction and the ratio of isocyanate to total mobile hydrogens is 1.0.

The resulting material is then intimately admixed with compounds produced according to Example II or compositions produced according to Example III at levels of 0.5%, 1.0%, 1.5%, 2.0% and 4.0% giving rise to textile finishes which when coated onto textiles during washing or finishing yield sandalwood, woody aroma profiles with musky background.

EXAMPLE X

PERFUMED FABRIC WHITENERS

Azastilbene fluorescent whiteners which are perfumed are prepared by reacting aldehydes with dialkyl (substituted pyridinyl) methyl phosphonates and having the structure:

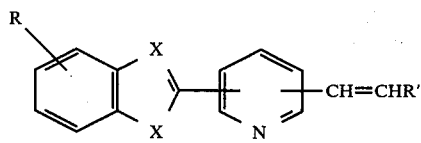

wherein X is oxygen; R is chloro; R' is phenyl. The preparation is according to Japanese Patent 79/34-780 published on Oct. 29, 1979 and assigned to the Mitsui Toatsu Chemical Inc.. To this whitener is added at the levels of 0.05%, 0.1%, 0.15%, 0.2%, 0.3% and 0.5%, compounds and compositions prepared according to Examples II and III. The whiteners have imparted thereto aromas which can be described as sandalwood and woody with musky backgrounds. An intense long-lasting aroma is prepared using the mixture of compounds derived from peak "3" of the GLC profile of FIG. 4 which peak contains compounds having the structures:

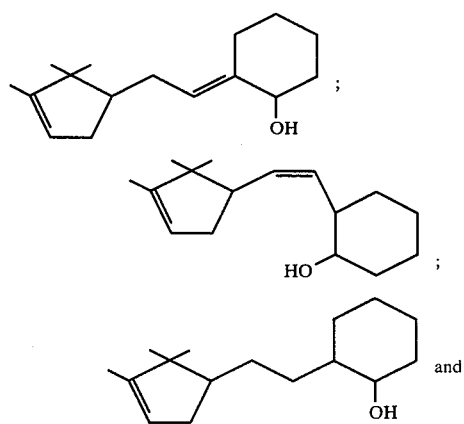

What is claimed is:
1. The compound having the structure:

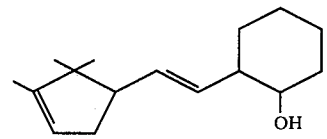

2. A mixture of compounds having the structures:

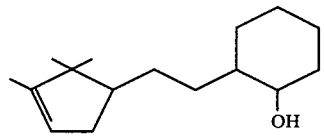

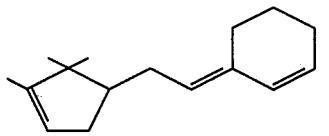

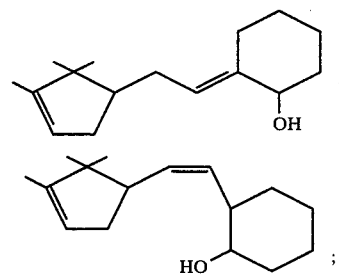

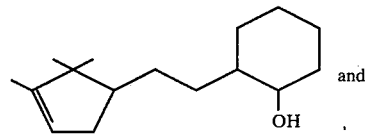

3. A process for augmenting or enhancing the organoleptic properties of a consumable material selected from the group consisting of perfume compositions, colognes and perfumed articles comprising the step of adding to said consumable material an organoleptic property-augmenting or enhancing quantity of at least one material selected from the group consisting of:

(i) The compound having the structure:

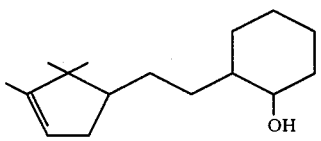

(ii) A mixture of compounds having the structures:

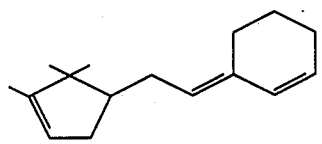

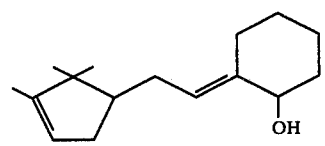

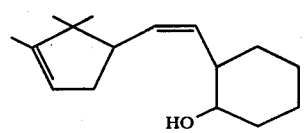

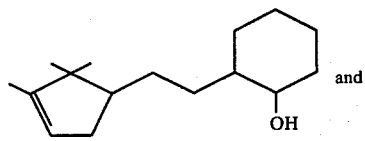

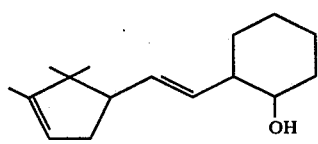
and (iii) A mixture of compounds having the structures:

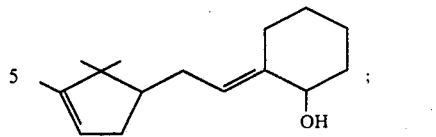

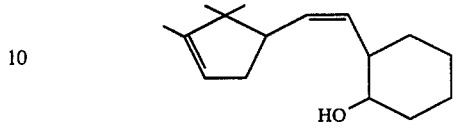

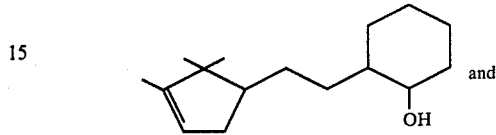
and

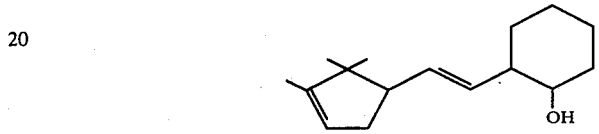

4. A process for augmenting or enhancing the organoleptic properties of a consumable material selected from the group consisting of perfume compositions, colognes and perfumed articles comprising the step of adding to said consumable material an organoleptic property augmenting or enhancing quantity of the compound having the structure:

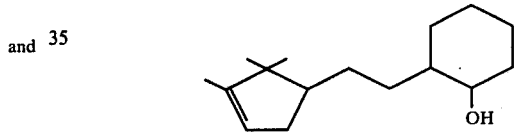

* * * * *